(12) United States Patent
Fujito

(10) Patent No.: US 10,564,135 B2
(45) Date of Patent: Feb. 18, 2020

(54) CHROMATOGRAPH MASS SPECTROMETER

(71) Applicant: SHIMADZU CORPORATION, Kyoto-shi, Kyoto (JP)

(72) Inventor: Yuka Fujito, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 16/091,629

(22) PCT Filed: Apr. 8, 2016

(86) PCT No.: PCT/JP2016/061539
§ 371 (c)(1),
(2) Date: Oct. 5, 2018

(87) PCT Pub. No.: WO2017/175379
PCT Pub. Date: Oct. 12, 2017

(65) Prior Publication Data
US 2019/0154642 A1 May 23, 2019

(51) Int. Cl.
*H01J 49/00* (2006.01)
*G01N 30/72* (2006.01)

(52) U.S. Cl.
CPC .......... *G01N 30/72* (2013.01); *H01J 49/0045* (2013.01); *H01J 49/00* (2013.01)

(58) Field of Classification Search
CPC .......... G01N 30/72; H01J 49/00; H01J 49/04; H01J 49/0045; H01J 49/26
See application file for complete search history.

(56) References Cited

U.S. PATENT DOCUMENTS 9,638,677 B2 * 5/2017 Kobayashi ............. G01N 30/72
2014/0117227 A1 * 5/2014 Fujita ..................... H01J 49/004
250/286

(Continued)

FOREIGN PATENT DOCUMENTS

JP 2011-141220 A 7/2011
WO 2016002046 A1 1/2016

OTHER PUBLICATIONS

Communication issued Mar. 11, 2019 by the European Patent Office in application No. 16897935.9.

(Continued)

*Primary Examiner* — Wyatt A Stoffa
(74) *Attorney, Agent, or Firm* — Sughrue Mion, PLLC

(57) ABSTRACT

A chromatograph mass spectrometer for performing SIM measurement and/or MRM measurement on a plurality of target components includes: a memory 41 for previously storing measurement conditions created for each of the target components, the measurement conditions including an SIM measurement ion or an MRM transition, a measurement execution time period, and an initial dwell time; a measurement time divider 42 for dividing an entire measurement time into a plurality of partial time periods having different combinations of measurements executed in the same time period; a time period input receiver 43 for receiving an input for selecting one of the partial time periods; a sensitivity information input receiver 45 for receiving an input of sensitivity information relating to the measurement conditions executed in the selected partial time period; a dwell time calculator 47 for calculating a changed dwell time by increasing or reducing the initial dwell time according to details of the input of the sensitivity information; and a loop time calculator 48 for calculating a loop time (Continued)

from the changed dwell time and outputting the calculated loop time.

4 Claims, 4 Drawing Sheets

(56) References Cited

U.S. PATENT DOCUMENTS

2015/0247829 A1* 9/2015 Sumiyoshi ......... G01N 30/8651
   250/288
2017/0138916 A1* 5/2017 Sumiyoshi ......... G01N 30/7233
2018/0166265 A1* 6/2018 Geromanos ............ G01N 30/72

OTHER PUBLICATIONS

Written Opinion for PCT/JP2016/061539 dated Jun. 14, 2016 [PCT/ISA/237].

* cited by examiner

Fig. 2
| TARGET COMPONENT | EVENT | CHANNEL | m/z | EXECUTION TIME PERIOD (min.) | INITIAL DWELL TIME (msec.) |
|---|---|---|---|---|---|
| COMPONENT A | 1 | 1 | A1>a1 | 2.0-5.0 | 5 |
| COMPONENT A | 1 | 2 | A2>a2 | 2.0-5.0 | 5 |
| COMPONENT B | 2 | 1 | B1>b1 | 15.0-20.0 | 5 |
| COMPONENT B | 2 | 2 | B2>b2 | 15.0-20.0 | 5 |
| COMPONENT C | 3 | 1 | C1>c1 | 3.5-6.5 | 5 |
| COMPONENT C | 3 | 2 | C2>c2 | 3.5-6.5 | 5 |
| COMPONENT D | 4 | 1 | D>d | 10.0-12.0 | 5 |
| COMPONENT E | 5 | 1 | E>e | 10.0-12.0 | 5 |
| ... | ... | ... | ... | ... | ... |
Fig. 3A
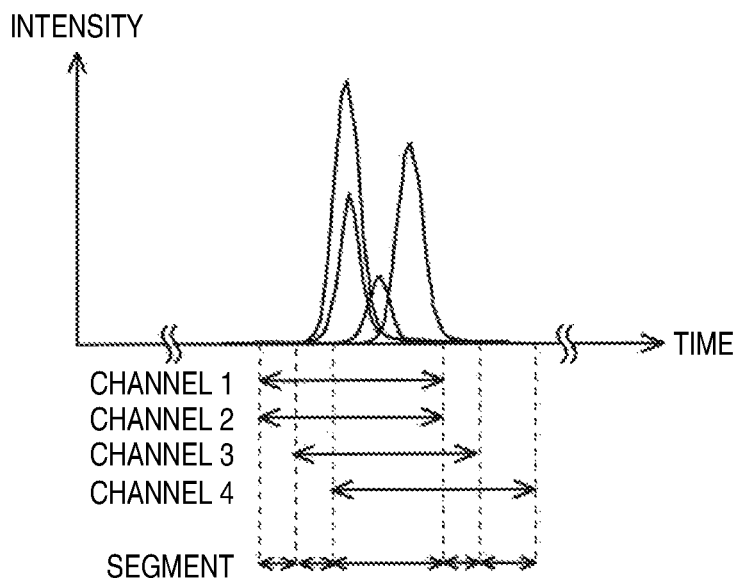
Fig. 3B
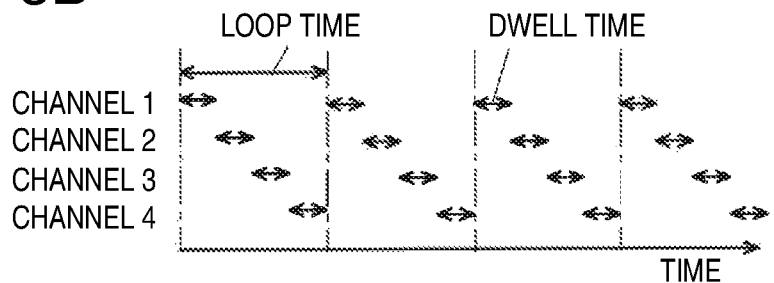

Fig. 4A

| SEGMENT | 1 | 2 | 3 | ... | 15 | ... |
|---|---|---|---|---|---|---|
| START TIME (min.) | 0.143- | 0.323- | 0.359- | ... | 10.51- | ... |
| NUMBER OF CHANNELS | 1 | 2 | 3 | ... | 20 | ... |
| LOOP TIME (msec) | 5.0 | 10.0 | 15.0 | ... | 100.0 | ... |
| DWELL TIME (msec) | 5.0 | 5.0 | 5.0 | ... | 5.0 | ... |

Fig. 4B

| SEGMENT | 1 | 2 | 3 | ... | 15 | ... |
|---|---|---|---|---|---|---|
| START TIME (min.) | 0.143- | 0.323- | 0.359- | ... | 10.51- | ... |
| NUMBER OF CHANNELS | 1 | 2 | 3 | ... | 20 | ... |
| LOOP TIME (sec) | 5.0 | 10.0 | 15.0 | ... | 175.0 | ... |
| DWELL TIME (msec) | 5.0 | 5.0 | 5.0 | ... | 5.0 / 20.0 | ... |

Fig. 5A

| | |  |
|---:|:---:|:---|
| SEGMENT | 15 | |
| START TIME (min.) | 10.51- | |
| NUMBER OF CHANNELS | 20 | ch. |
| CURRENT LOOP TIME | 100 | msec. |
| MAXIMUM LOOP TIME (TARGET VALUE) | 700 | msec. |
| SET MAXIMUM DWELL TIME | 20 | msec. |
| SET MINIMUM DWELL TIME | 3 | msec. |
| DWELL TIME CHANGE | DEFAULT | |

| TRANSITION | | | SENSITIVITY | CURRENT DWELL TIME (msec.) | CHANGED DWELL TIME (msec.) |
|---|---|---|---|---|---|
| EVENT | CHANNEL | m/z | | | |
| 1 | 1 | 201>105 | — | 5 | 5 |
| 1 | 2 | 201>153 | — | 5 | 5 |
| 2 | 1 | 343>123 | ↑ | 5 | 20 |
| 2 | 2 | 343>100 | — | 5 | 5 |
| 3 | 1 | 531>124 | ↑ | 5 | 20 |
| 3 | 2 | 531>220 | — | 5 | 5 |
| 4 | 1 | 432>157 | ↓ | 5 | 3 |
| 5 | 1 | 420>121 | ↓ | 5 | 3 |
| ... | ... | ... | ... | ... | ... |

CHANGED LOOP TIME | 175 | msec

Fig. 5B

| | | |
|---:|:---:|:---|
| SEGMENT | 15 | |
| START TIME (min.) | 10.51- | |
| NUMBER OF CHANNELS | 20 | ch. |
| CURRENT LOOP TIME | 100 | msec. |
| MAXIMUM LOOP TIME (TARGET VALUE) | 700 | msec. |
| SET MAXIMUM DWELL TIME | | msec. |
| SET MINIMUM DWELL TIME | | msec. |
| DWELL TIME CHANGE | MANUAL | |

| TRANSITION | | | SENSITIVITY | CURRENT DWELL TIME (msec.) | CHANGED DWELL TIME (msec.) |
|---|---|---|---|---|---|
| EVENT | CHANNEL | m/z | | | |
| 1 | 1 | 201>105 | — | 5 | 5 |
| 1 | 2 | 201>153 | — | 5 | 5 |
| 2 | 1 | 343>123 | ↑ | 5 | 20 |
| 2 | 2 | 343>100 | — | 5 | 5 |
| 3 | 1 | 531>124 | ↑ | 5 | 20 |
| 3 | 2 | 531>220 | — | 5 | 5 |
| 4 | 1 | 432>157 | ↓ | 5 | 3 |
| 5 | 1 | 420>121 | ↓ | 5 | 3 |
| ... | ... | ... | ... | ... | ... |

CHANGED LOOP TIME | 175 | msec

CHROMATOGRAPH MASS SPECTROMETER

TECHNICAL FIELD

The present invention relates to a chromatograph mass spectrometer for temporally separating a plurality of known target components contained in a sample in a chromatograph and performing selective ion monitoring measurement and/or multiple reaction monitoring measurement on the target components.

BACKGROUND ART

There is a technique called MS/MS analysis (tandem mass spectrometry) as a technique of mass spectrometry used for identification and quantitative determination of a known target component contained in a sample. The MS/MS analysis is performed using, for example, a mass spectrometer (e.g., a tandem quadrupole mass spectrometer) including a front-stage mass separator for sorting out a precursor ion, a fragmentation unit, such as a collision cell, for fragmenting the precursor ion to produce product ions, and a rear-stage mass separator for sorting out the product ions.

Multiple reaction monitoring (MRM) measurement is one of measurements in the MS/MS analysis. In the MRM measurement, mass-to-charge ratios of ions allowed to pass through the front-stage mass separator and the rear-stage mass separator are fixed, and the intensity of a specific product ion produced from a specific precursor ion is measured. The pair of the precursor ion and the product ion is called an MRM transition. In the MRM measurement, ions derived from components but not to be measured and foreign components and neutral particles that have not been ionized are removed by the two front-stage and rear-stage mass separators. Thus, it is possible to obtain an ion intensity signal with a large S/N ratio.

According to such an advantage, the MRM measurement is used for analysis of a sample containing a plurality of known target components such as a sample taken from soil or a tissue-derived sample. A chromatograph mass spectrometer combining a chromatograph (a gas chromatograph or a liquid chromatograph) with a mass spectrometer having the above configuration is used for batch analysis of such many components. A plurality of target components contained in a sample are temporally separated in a column of the chromatograph and introduced into the mass spectrometer, and the MRM measurement is performed on each of the target components.

When the chromatograph mass spectrometer executes the MRM measurement, one or more MRM measurement conditions are previously determined for each of the target components. The MRM measurement conditions include an MRM measurement time period which is a time period for executing the measurement and an MRM transition used in the measurement. Each MRM measurement time period is determined so that the MRM measurement time period includes the chromatographic retention time of the target component to be measured, and the MRM transition is determined with reference to database. A set of one or more MRM measurements performed for one target component is called an event. Each of the MRM measurements is called a channel.

In a batch analysis of a plurality of components, the plurality of MRM measurement time periods often overlap each other partially or entirely. In such a case, an operation for sequentially executing the plurality of channels set in the overlapping time period one by one for a predetermined time is repeatedly performed. The execution time for executing each channel once is called a dwell time, and a total time required for executing the plurality of channels once in the same time period is called a loop time. When the batch analysis of the plurality of components is planned, for example, a user sets an appropriate loop time, and the set loop time is divided by the number of channels executed in the same time period to determine a dwell time.

A mass chromatogram corresponding to each channel is obtained by executing the measurement of the sample under the MRM measurement conditions determined as described above. Normally, in an MRM measurement, an MRM transition with which target components can be measured with the highest sensitivity (that is, having the highest efficiency of producing product ions) is selected. However, the sensitivity differs between target components. Thus, when an equal dwell time is allotted to each channel, a peak intensity may be too small in a mass chromatogram obtained in some channels to perform quantitative determination.

Thus, in a conventional technique, a user checks a mass chromatogram acquired in each channel, and extends the dwell time of a channel having a small mass peak intensity in order to create adequate MRM measurement conditions under which target components can be measured with high sensitivity in all channels.

CITATION LIST

Patent Literature

Patent Literature 1: JP 2011-141220 A

SUMMARY OF INVENTION

Technical Problem

However, when the dwell time of each channel is extended, the loop time including the channel is also extended. The loop time is, in other words, a time interval of data acquisition in each channel. Thus, when the time interval is extended, the number of measurement points for one peak becomes insufficient. Accordingly, the peak reproducibility of the mass chromatogram is deteriorated, and it becomes hard to perform an accurate quantitative determination of a target component.

The case of an MRM measurement is described above just as an example, and there is a similar problem in the case of selective ion monitoring measurement (SIM measurement) and in the case where both the SIM measurement and the MRM measurement are performed.

It is an object of the present invention to provide a chromatograph mass spectrometer capable of determining, based on mass chromatogram data obtained by performing an SIM measurement and/or one or more MRM measurements under one or more measurement conditions, an appropriate execution time for executing each SIM measurement and/or each MRM measurement once (a dwell time of each channel) for each of a plurality of target components contained in a sample.

Solution to Problem

The present invention developed for solving the above-described problem provides a chromatograph mass spectrometer for temporally separating a plurality of target components contained in a sample and performing selective ion monitoring measurement and/or multiple reaction monitoring measurement on each of the target components under one or more measurement conditions, the chromatograph mass spectrometer including:

a) a memory for previously storing measurement conditions created for each of the target components, the measurement conditions including an SIM measurement ion which is an ion measured in the selective ion monitoring measurement or an MRM transition which is a pair of precursor and product ions used in the multiple reaction monitoring measurement, an execution time period of the measurement conditions, and an initial dwell time which is an initial value of an execution time of one measurement:

b) a measurement time divider for dividing an entire measurement time from a start to an end of the measurement of the sample into a plurality of partial time periods having different combinations of the selective ion monitoring measurement and/or the multiple reaction monitoring measurement executed in the same time period;

c) a time period input receiver for receiving an input by a user for selecting one of the partial time periods:

d) a sensitivity information input receiver for receiving an input of sensitivity information relating to measurement conditions executed in the selected partial time period;

e) a dwell time calculator for calculating a changed dwell time by increasing or reducing the initial dwell time according to details of the input of the sensitivity information; and f) a loop time calculator for calculating a loop time from the changed dwell time and outputting the calculated loop time.

For example, for the input of the sensitivity information, the "↑" key on the keyboard can be used to extend the dwell time to enhance the sensitivity, and the "↓" key can be used to shorten the dwell time to lower the sensitivity. No key operation may indicate that the dwell time is not extended or shortened. In case of the operation of "↑" key, the dwell time calculator extends the initial dwell time of a measurement condition by a predetermined unit time, and in case of the operation of "↓" key, the dwell time calculator shortens the initial dwell time of a measurement condition by a predetermined unit time. Alternatively, the sensitivity information may be input as a numerical value, and the dwell time calculator may add the input numerical value to (or subtract the input numerical value from) the initial dwell time to obtain the changed dwell time.

In the chromatograph mass spectrometer according to the present invention, the entire measurement time is divided into a plurality of partial time periods having different combinations of measurements executed in the same time period based on measurement conditions previously stored in the memory. The user selects one of the partial time periods, and checks a peak of a mass chromatogram obtained by each measurement (channel) using the measurement conditions stored in the memory. When, for example, "↑" key is operated for a channel that needs raising the sensitivity and "↓" key is operated for a channel having no problem with lowering the sensitivity, the changed dwell time reflecting these inputs of sensitivity information keys is created, and the loop time based on the changed dwell time is calculated and output. The user can determine an appropriate dwell time by checking the output loop time and re-inputting sensitivity information when the output loop time is too long.

Preferably, the chromatograph mass spectrometer according to the present invention further includes:

g) a display unit; and h) a measurement condition display unit for displaying the SIM measurement ion or MRM transition relating to each of the measurement conditions and the initial dwell time on the display unit, and the loop time calculator displays the loop time on the display unit.

In the chromatograph mass spectrometer of the above aspect, the user can visually check measurement conditions executed in the designated partial time period and the loop time based on the changed dwell time at once on a screen of the display unit.

Further, preferably, in the chromatograph mass spectrometer according to the present invention, a maximum loop time is previously stored in the memory, and the chromatograph mass spectrometer further includes i) a reset presenter for prompting the user to change the sensitivity information or the changed dwell time when the loop time calculated by the loop time calculator is longer than the maximum loop time.

In the chromatograph mass spectrometer of the above aspect including the reset presenter, when an updated loop time becomes longer than the maximum loop time, the reset presenter prompts the user to change the input. Thus, it is possible to more reliably prevent a deterioration in the peak reproducibility of the chromatogram caused by an excessively long loop time.

Further, in the chromatograph mass spectrometer according to the present invention, mass chromatogram data obtained by executing the measurement under the measurement conditions stored in the memory may be stored in the memory, and the chromatograph mass spectrometer may further include j) a measurement sensitivity calculator for calculating a measurement sensitivity of an ion in the measurement based on the mass chromatogram data corresponding to each of the measurement conditions and inputting the sensitivity information based on the measurement sensitivity.

For example, an intensity value of a peak in the mass chromatogram data or an area value of a peak of a mass chromatogram created from the data can be used as the measurement sensitivity of the ion.

The dwell time of each channel can be more easily determined by using the chromatograph mass spectrometer of the above aspect including the measurement sensitivity calculator.

Advantageous Effects of Invention

Using the chromatograph mass spectrometer according to the present invention makes it possible to easily determine an appropriate execution time for each measurement condition used in an SIM measurement or an MRM measurement based on a mass chromatogram obtained in an SIM measurement or an MRM measurement performed in advance.

BRIEF DESCRIPTION OF DRAWINGS

FIG. 2 illustrates an example of a method file used in the chromatograph mass spectrometer of the present embodiment.

FIGS. 3A and 3B are diagrams for describing a channel execution time, a segment, a dwell time, and a loop time.

FIGS. 4A and 4B illustrate examples of a segment list display window in the present embodiment.

FIGS. 5A and 5B illustrate examples of a measurement condition display window in the present embodiment.

DESCRIPTION OF EMBODIMENTS

Figure 1:
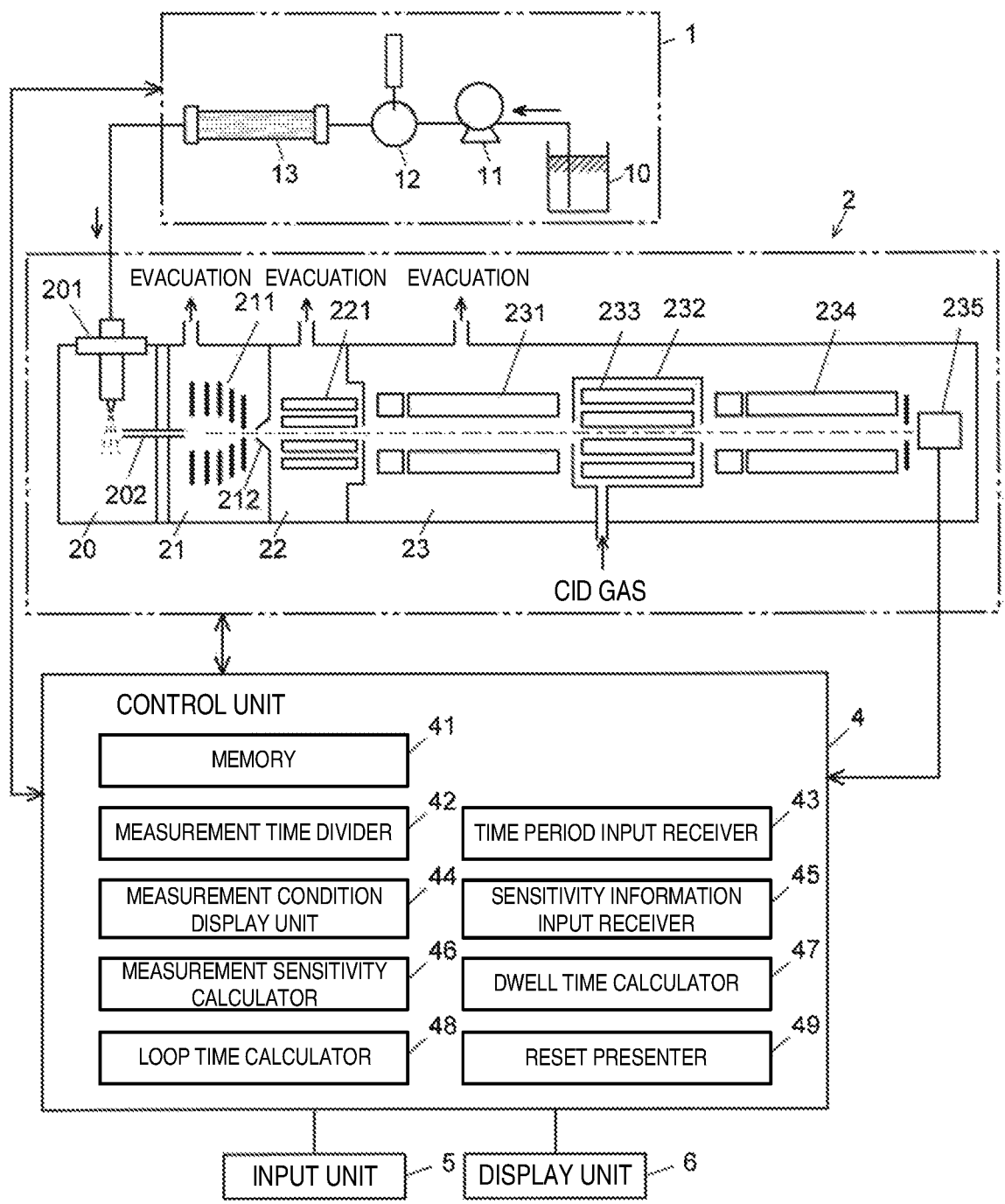
FIG. 1 is a main part configuration diagram of one embodiment of a chromatograph mass spectrometer according to the present invention.

Hereinbelow, an embodiment of a chromatograph mass spectrometer according to the present invention will be described with reference to the drawings. FIG. 1 is a main part configuration diagram of the chromatograph mass spectrometer of the present embodiment.

The chromatograph mass spectrometer of the present embodiment is a liquid chromatograph mass spectrometer which includes a liquid chromatograph unit 1, a mass spectrometer unit 2, and a control unit 4 for controlling the operations of the liquid chromatograph unit 1 and the mass spectrometer unit 2.

In the liquid chromatograph mass spectrometer of the present embodiment, the liquid chromatograph unit 1 includes a mobile-phase container 10 for holding a mobile phase, a pump 11 for drawing the mobile phase and feeding the drawn mobile phase at a fixed flow rate, an injector 12 for injecting a predetermined amount of sample liquid into the mobile phase, and a column 13 for temporally separating various compounds contained in the sample.

The mass spectrometer unit 2 has the configuration of a multistage differential pumping system including an ionization chamber 20 maintained at a substantially atmospheric pressure, a high-vacuum analysis chamber 23 evacuated by a vacuum pump (not illustrated), and first and second intermediate vacuum chambers 21 and 22 whose degrees of vacuum are increased in a stepwise manner, the first and second intermediate vacuum chambers 21 and 22 being disposed between the ionization chamber 20 and the analysis chamber 23. The ionization chamber 20 is provided with an electrospray ionization probe (ESI probe) 201 for spraying a sample solution while electrically charging the sample solution. The ionization chamber 20 communicates with the first intermediate vacuum chamber 21 in the subsequent stage through a thin heated capillary 202. The first intermediate vacuum chamber 21 and the second intermediate vacuum chamber 22 are separated by a skimmer 212 which has a small hole at its apex. The first intermediate vacuum chamber 21 and the second intermediate vacuum chamber 22 are respectively provided with ion guides 211 and 221 for transporting ions to the subsequent stage while focusing the ions. The analysis chamber 23 is provided with a collision cell 232 inside which a multi-pole ion guide (q2) 233 is disposed, a front-stage quadrupole mass filter (Q1) 231 for separating ions according to their mass-to-charge ratios, a rear-stage quadrupole mass filter (Q3) 234 for similarly separating ions according to their mass-to-charge ratios, and an ion detector 235. The collision cell 232 is disposed between the front-stage quadrupole mass filter (Q1) 231 and the rear-stage quadrupole mass filter (Q3) 234.

CID gas, such as argon or nitrogen, is appropriately supplied into the collision cell 232. Each of the quadrupole mass filters 231 and 234 includes a pre-rod electrode for correcting a disturbance in an electric field at its entrance terminal in the preceding stage of a main rod electrode. A voltage different from a voltage applied to the main rod electrode can be applied to the pre-rod electrode.

In the mass spectrometer unit 2, for example, selective ion monitoring (SIM) measurement, product ion scan measurement, and multiple reaction monitoring (MRM) measurement can be performed. In the SIM measurement, the front-stage quadrupole mass filter (Q1) 231 does not sort out ions (does not function as a mass filter), and a mass-to-charge ratio of an ion allowed to pass through the rear-stage quadrupole mass filter (Q3) 234 is fixed to detect the ion having the mass-to-charge ratio.

On the other hand, in the MS/MS scan measurement (product ion scan measurement) and the MRM measurement, the front-stage quadrupole mass filter (Q1) 231 and the rear-stage quadrupole mass filter (Q3) 234 both function as a mass filter. Only ion set as precursor ion is allowed to pass through the front-stage quadrupole mass filter (Q1) 231. CID gas is supplied into the collision cell 232 in order to fragment the precursor ion and to produce product ions. The mass-to-charge ratio of an ion that passes through the rear-stage quadrupole mass filter (Q3) 234 is scanned in the MS/MS scan measurement and, on the other hand, fixed in the MRM measurement.

The control unit 4 includes a memory 41, and further includes, as functional blocks, a measurement time divider 42, a time period input receiver 43, a measurement condition display unit 44, a sensitivity information input receiver 45, a measurement sensitivity calculator 46, a dwell time calculator 47, a loop time calculator 48, and a reset presenter 49. The control unit 4 also has a function of controlling the operations of the members of the liquid chromatograph unit 1 and the mass spectrometer unit 2 and a function of applying a predetermined voltage to the members of the spectrometer unit 2 from a voltage application unit (not illustrated). The actual body of the control unit 4 is a personal computer, and a program previously installed in the computer is executed to cause each of the above functional blocks to function. An input unit 5 and a display unit 6 are connected to the control unit 4.

Hereinbelow, a procedure for determining conditions of performing the MRM measurement on a plurality of target components contained in a sample by the liquid chromatograph mass spectrometer of the present embodiment will be described.

First, a user determines, for each of the target components contained in the sample, initial measurement conditions including an MRM transition (a pair of precursor and product ions) mass-to-charge ratio used in the MRM measurement, an execution time period of the measurement using the MRM transition, and an initial dwell time, and stores a method file describing the initial measurement conditions in the memory 41.

FIG. 2 illustrates an example of the initial measurement conditions. In FIG. 2, a set of one or more MRM measurements performed for one target component is called an event, and each of the MRM measurements is called a channel. A time for executing each channel once is called a dwell time, and a total time required for executing one or more channels set in the same time period once is called a loop time. In the present embodiment, an initial dwell time is uniformly set to 5 msec. However, a user may set an appropriate loop time, and the set loop time may be divided by the number of channels executed in the same time period to determine the initial dwell time.

The relationship between the execution time period of each channel, a segment, the dwell time, and the loop time will be described with reference to FIGS. 3A and 3B. As illustrated in FIG. 3A, when execution time periods of channels 1 to 4 are set in an overlapping manner, the measurement time divider 42 divides the entire measurement time into segments for respective combinations of the overlapping channels. In the example of FIG. 3A, the entire measurement time is divided into five segments; a segment 1 in which the channels 1 and 2 are executed; a segment 2 in which the channels 1 to 3 are executed; a segment 3 in which the channels 1 to 4 are executed; a segment 4 in which the channels 3 and 4 are executed; and a segment 5 in which only the channel 4 is executed.

In each segment, the channels (MRM measurements) set in the segment are executed once, and the execution is repeated. For example, in the segment 3, the channels 1 to 4 are sequentially executed once, and the execution is repeated as illustrated in FIG. 3B.

When a user commands the execution of the measurement, the method file is read from the memory 41, and the MRM measurement for each target component is executed under the initial measurement conditions described in the method file. Mass chromatogram data obtained in each MRM measurement (each channel) is stored in the memory 41.

In general, the channels have different peak intensities as illustrated in FIG. 3A in the mass chromatogram data obtained in the above procedure. That is, the channels have different sensitivities for the target components. Thus, an operation for changing the dwell time is required to reduce variations in the sensitivity for the plurality of target components. The operation mainly extends the dwell time for the purpose of raising a detection limit of a component detected with low sensitivity. On the other hand, the dwell time may also be shortened for a component detected with high sensitivity as long as the measurement is not hindered.

When the user commands the start of the operation for changing the dwell time, the time period input receiver 43 reads the method file stored in the memory 41 and displays, for each of the segments divided by the measurement time divider 42, a list of a start time of the segment, the number of channels to be executed, the loop time, and the dwell time of each of the channels to be executed on the display unit 6, and prompts the user to input a time period. FIG. 4A illustrates an example of a segment list display window.

Although, in FIG. 4A, only some of the segments are displayed, all of the segments can be displayed by scrolling the window in a horizontal direction so that the user can check them. FIG. 4A illustrates a display reflecting the initial measurement conditions. Thus, the loop time is a value obtained by multiplying the number of channels by 5 msec.

When the user selects any one of the segments (here, a segment 15) through the input unit 5, the measurement condition display unit 44 displays a list of events and channels (a list of measurement conditions) set in the selected segment (segment 15) on the display unit 6.

As illustrated in FIG. 5A, a start time of channels set in the segment 15, the number of channels to be executed in the segment 15, a current loop time, a maximum loop time (target value), a set maximum dwell time, a set minimum dwell time, and a mode selection field (default, manual, or automatic) for changing a dwell time are displayed in an upper part of the measurement condition list display window. In the current loop time field, 100 msec which is obtained by multiplying the number of channels (20) by the initial dwell time (5 msec) is displayed. Although an initial value (700 msec) is input as the maximum loop time (target value), the initial value can be appropriately changed by the user. The loop time corresponds to a data acquisition interval in each channel. Normally, in order to correctly reproduce a peak of a chromatogram, the peak needs to include ten or more measurement points. Thus, the user checks a peak width of a mass chromatogram acquired under the initial measurement conditions, and a value obtained by dividing the peak width by 10 (or a time slightly shorter than the value) can be set as the maximum loop time (target value).

Further, a list of execution conditions of channels executed in the selected segment (segment 15) is displayed in a lower part of the window. The list includes an event number, a channel number, an MRM transitions (m/z) used in the channel, a sensitivity input field, a current dwell time display field, and a changed dwell time display field.

The user checks the mass chromatogram of each channel obtained in the measurement of the sample using the initial measurement conditions. Then, the user inputs sensitivity information of "↑" in the sensitivity input field for a channel that has been determined to require increasing the sensitivity and inputs sensitivity information of "↓" in the sensitivity input field for a channel that has been determined to have no problem with reducing the sensitivity. When "↑" is input in the sensitivity input field, the dwell time of the channel is changed from the initial value of 5 msec to 20 msec (the above set maximum dwell time) and displayed in the changed dwell time display field. On the other hand, when "↓" is input in the sensitivity input field, the dwell time of the channel is changed to 3 msec (the above set minimum dwell time) and displayed in the changed dwell time display field. Then, every time the dwell time is changed, the changed loop time is recalculated and displayed. An input form to the sensitivity input field can be appropriately modified.

The input of the sensitivity information is not limited to the above combination of "↑" and "↓", and an appropriate combination, such as "+" and "−", can be used. Further, a plurality of stages may be set between the initial value and the maximum/minimum dwell time. A plurality of alternatives may be displayed in a pull-down menu, and the user may select one of the alternatives.

FIG. 5B illustrates an example in the case where the manual mode is selected as a mode of the dwell time change. In this window, when "↑" or "↓" is input in the sensitivity input field of a certain channel, a numerical value input of a changed dwell time of the channel is enabled. The user can increase (or reduce) the sensitivity by inputting an appropriate numerical value. Alternatively, the numerical value input of the changed dwell time may be enabled regardless of an input to the sensitivity input field.

In either the case where the dwell time is changed by the default mode or the case where the dwell time is changed by the manual mode, every time "↑" is input or a changed dwell time longer than the current dwell time is input, the changed loop time is extended. When the changed loop time becomes longer than the maximum loop time (target value) displayed in the upper part of the window, the reset presenter 49 displays a message prompting the user to check the changed dwell time on the display unit 6. The maximum loop time (target value) is merely a standard loop time, and it is possible to perform the measurement itself with a loop time longer than the maximum loop time. However, since the measurement interval of each channel becomes too long, the peak reproducibility of the chromatogram may be deteriorated. In the present embodiment, the deterioration in the peak reproducibility of the chromatogram can be avoided by prompting the user to check the changed dwell time (and the changed loop time calculated based on the changed dwell time) by the reset presenter 49.

When the automatic mode is selected as the dwell time change mode, the measurement sensitivity calculator 46 calculates a peak intensity (or a peak area value) from the mass chromatogram of each channel which is acquired under the initial measurement conditions and stored in the memory 41 and automatically inputs the calculated numerical value to the sensitivity input field as sensitivity information of each channel.

When a numerical value is input as the sensitivity information of each channel, the dwell time calculator 47 calculates a changed dwell time by distributing the maximum loop time (target value) to each channel according to the numerical value of the sensitivity information and displays the calculated time in the changed dwell time field. Specifically, for example, the changed dwell time is calculated by distributing the maximum loop time (target value) proportional to the inverse of the measurement sensitivity. When the automatic mode is selected as the dwell time change mode, the changed dwell time can be determined without a numerical value input to the sensitivity information and the changed dwell time of each channel by the user.

In the mode (automatic mode) which automatically changes the dwell time, the dwell time may be changed in the following manner.

Thresholds (e.g., two thresholds) of one or more peak intensities are previously determined. The peak intensities are classified into three stages: high; medium; and low based on the relationship between the peak intensity of each channel and the two thresholds. The dwell time of a channel having a high peak intensity is shortened to 3 msec. The dwell time of a channel having a medium peak intensity is maintained at 5 msec. The dwell time of a channel having a low peak intensity is extended to 20 msec.

Further, the dwell time may be changed in the following manner. Mass peaks are ranked in descending order of the peak intensity. The dwell time of a predetermined percentage (e.g., 20%) of the channels in descending order of the peak intensity is shortened to 3 msec. The dwell time of a predetermined percentage (e.g., 40%) of the channels in ascending order of the peak intensity is extended to 20 msec. The dwell time of the other channels (the channels having a medium peak intensity) is maintained at 5 msec.

In the above configuration, the peak intensities are classified into three stages: high; medium; and low, and the dwell time of each channel is changed in accordance with the classification. It is needless to say that the peak intensities may also be classified into two stages or four or more stages. When the peak intensities are classified into a large number of stages, for example, a table associating each stage with the dwell time may be previously stored in the memory, and the dwell time of each channel classified based on the peak intensity may be changed in accordance with the table. Further, the thresholds or the percentages used in classifying the peak intensities into a plurality of stages may be determined by automatic allocation according to the number of channels in each segment in such a manner that the total dwell time falls within the maximum loop time (target value) in each segment.

The user can re-change (finely adjust) the changed dwell time of each channel which is obtained by selecting the default or automatic mode as the dwell time change mode, by changing the default or automatic mode to the manual mode after the changed dwell time of each channel is obtained in the default or automatic mode.

After the changed dwell time of each channel is determined for the selected segment, the user returns the window to the original segment selection window and determines the changed dwell time of each channel also for each of the other segments in a similar manner. FIG. 4B illustrates a display example of the segment selection window after the changed dwell time of each channel of the segment 15 is determined as described in the above embodiment. FIG. 4B shows that displays of the loop time and the dwell time have been updated for the segment 15. The display of the dwell time in FIG. 4B includes a minimum value and a maximum value of the dwell time in the channels executed in the segment 15.

After the changed dwell time of each channel is determined for all of the segments, a part relating to the dwell time in the initial measurement conditions stored in the memory 41 is changed to create actual measurement conditions, and a new method file describing the actual measurement conditions is stored in the memory 41.

As described above with reference to FIG. 3A, in general, each channel is set across a plurality of segments. That is, the same channel is often displayed in measurement condition windows of a plurality of segments. In such a case, preferably, an input to each field is disabled for a channel whose changed dwell time has already been determined or the user presses a reconfirmation button for lock release when the user inputs sensitivity information or a changed dwell time so as to prevent a changed dwell time determined in one segment from being overwritten in another segment.

The above embodiment is merely an example and can be appropriately changed along the technical concept of the present invention.

In the above embodiment, the case where only the MRM measurement is performed has been described as an example. However, the case where only the SIM measurement is performed or the case where both the MRM measurement and the SIM measurement are performed can be configured in a similar manner. Further, the liquid chromatograph mass spectrometer has been described above as an example. However, the above embodiment can be configured in a similar manner with a gas chromatograph mass spectrometer. Further, the illustrated windows are examples. Windows with an appropriate layout can be displayed on the display unit in accordance with the above description. Alternatively, some of the displays may be changed to voice output instead of the window display.

REFERENCE SIGNS LIST

1 . . . Liquid Chromatograph Unit
2 . . . Mass Spectrometer Unit
4 . . . Control Unit
41 . . . Memory
42 . . . Measurement Time Divider
43 . . . Time Period Input Receiver
44 . . . Measurement Condition Display Unit
45 . . . Sensitivity Information Input Receiver
46 . . . Measurement Sensitivity Calculator
47 . . . Dwell Time Calculator
48 . . . Loop Time Calculator
49 . . . Reset Presenter
5 . . . Input Unit
6 . . . Display Unit

The invention claimed is:

1. A chromatograph mass spectrometer for temporally separating a plurality of target components contained in a sample and performing selective ion monitoring measurement and/or multiple reaction monitoring measurement on each of the target components under one or more measurement conditions, the chromatograph mass spectrometer comprising:

a) a memory storing measurement conditions created for each of the target components, the measurement conditions including an SIM measurement ion which is an ion measured in the selective ion monitoring measurement or an MRM transition which is a pair of precursor and product ions used in the multiple reaction monitoring measurement, an execution time period of the measurement conditions, and an initial dwell time which is an initial value of an execution time of one measurement; and b) at least one control unit configured to
divide an entire measurement time from a start to an end of the measurement of the sample into a plurality of partial time periods having different combinations of the selective ion monitoring measurement and/or the multiple reaction monitoring measurement executed in a same time period;
receive an input by a user for selecting one of the partial time periods;
receive an input of sensitivity information relating to measurement conditions executed in the selected partial time period;
calculate a changed dwell time by increasing or reducing the initial dwell time according to details of the input of the sensitivity information; and
calculate a loop time from the changed dwell time and outputting the calculated loop time.

2. The chromatograph mass spectrometer according to claim 1, further comprising:
a display unit;
the at least one control unit is further configured to display the SIM measurement ion or MRM transition relating to each of the measurement conditions and the initial dwell time on the display unit, and
display the loop time on the display unit.

3. The chromatograph mass spectrometer according to claim 1, wherein
a maximum loop time is stored in the memory, and
the at least one control unit is further configured to prompt the user to change the sensitivity information or the changed dwell time when the calculated loop time is longer than the maximum loop time.

4. The chromatograph mass spectrometer according to claim 1, wherein
mass chromatogram data obtained by executing the measurement under the measurement conditions stored in the memory is stored in the memory, and
the at least one control unit is further configured to calculate a measurement sensitivity of an ion in the measurement based on the mass chromatogram data corresponding to each of the measurement conditions and inputting the sensitivity information based on the measurement sensitivity.

* * * * *